(12) United States Patent
Wagner et al.

(10) Patent No.: US 6,403,361 B1
(45) Date of Patent: *Jun. 11, 2002

(54) ENZYMATIC METHOD FOR MODIFICATION OF RECOMBINANT POLYPEPTIDES

(75) Inventors: Fred W. Wagner, Walton; Jay Stout, Lincoln; Dennis Henriksen, Lincoln; Bruce Partridge, Lincoln; Shane Manning, Lincoln, all of NE (US)

(73) Assignee: Restoragen, Inc., Lincoln, NE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/505,991

(22) Filed: Feb. 17, 2000

Related U.S. Application Data

(63) Continuation of application No. 08/967,374, filed on Nov. 7, 1997, now Pat. No. 6,037,143, which is a continuation of application No. 08/520,485, filed on Aug. 29, 1995, now abandoned, which is a division of application No. 08/470,220, filed on Jun. 6, 1995, now Pat. No. 5,507,826, and a division of application No. 08/095,162, filed on Jul. 20, 1993, now Pat. No. 5,512,459.

(51) Int. Cl.$^7$ .......................... C12N 1/20; A01N 37/18; A61K 38/00; C07H 21/04
(52) U.S. Cl. .............................. 435/252.3; 435/320.1; 435/325; 514/2; 530/300; 536/23.4; 536/23.5
(58) Field of Search .................... 435/252.3, 252.33, 435/325, 320.1; 514/2; 530/300, 308, 350; 536/23.4, 23.5, 23.51

(56) References Cited

U.S. PATENT DOCUMENTS

| | | | |
|---|---|---|---|
| 4,710,382 A | 12/1987 | Recker | |
| 5,118,666 A | 6/1992 | Habener | |
| 5,120,712 A | 6/1992 | Habener | |
| 5,234,820 A | 8/1993 | Wagner et al. | |
| 5,279,954 A | 1/1994 | Wagner et al. | |
| 5,595,887 A | * 1/1997 | Coolidge et al. | 435/69.7 |
| 6,051,399 A | * 4/2000 | Stout et al. | 435/69.1 |
| 6,127,150 A | * 10/2000 | Coolidge et al. | 435/69.7 |

FOREIGN PATENT DOCUMENTS

| | | |
|---|---|---|
| EP | 0 485475 | 11/1991 |
| EP | 0490249 | 6/1992 |
| WO | WO 90/11296 | 10/1990 |

OTHER PUBLICATIONS

Agarwal et al. "Tight–Binding Inhibitors—IV, Inhibition of Adenosine Deaminases By Various Inhibitors", *Biochemical Pharm.*, 26: 359–367 (1977).
Barker et al. "Monosaccharides Attached to Agarose," *Methods Enzymol.*, 34: 317–328 (1974).
Bethell et al. "A Novel Method of Activation of Cross–Linked Agaroses with 1,1'–Carbonyldiimidazole Which Gives a Matrix for Affinity Chromatography Devoid of Additional Charged Groups," *J. Biol. Chem.*, 254: 2572–2574 (1979).
Bongers et al. "Comparison of Enzymatic Semisythesis of Peptide Amides: Human Growth Hormone Releasing Factor and Analogs," *Biomed. Biochem, Acta.*, 50: S157–62 (1991).
Bongers et al. "Semisynthesis of Human Growth Hormone–Releasing Factor By Trypsin Catalyzed Coupling of Leucine Amide to a C–Terminal Acid Precursor," *Int. J. Peptide Protein Res.*, 40: 268–273 (1992).
Canova–Davis et al. "Transpeptidation During the Analytical Proteolysis of Proteins," *Chemical Abstracts, No. 67959*, 115:429 (1991), (see Abstract & Anal Biochem., 196: 39–45 (1991)).
Carter et al. American Chemical Society 0097–6156/90/ 0427: 181–193 (1990).
Chang et al. "Thrombin Specifity", *Eur. J. Biochem.*, 151: 217–224 (1985).
Cha et al. "Tight Binding Inhibitors—II, Non–Steady State Nature of Inhibition of Milk Xanthine Oxidase By Allopurinol and Alloxanthine and of Human Erythrocytic Adenosine Deaminase by Coformycin," *Biochemical Pharm.*, 24: 2187–2197 (1978).
Cha et al. "Kinetic Parameters of Dihydrofolate Reductase Inhibited by Methotrexate, An Example of Equilibrium Study," *Biochemical Pharm.*, 30: 1507–1515 (1981).
Colman et al., "Hemostasis and Thrombosis," J.B. Lippincott Company, Philadelphia, PA. (1987).
Degrado et al. "The Design, Synthesis, and Characterization of Tight–Binding Inhibitors of Calmodulin," *J. Cellular Biochem.*, 29: 83–93 (1985).
Engels et al. "Enzymatic Amidation of Recombinant (Leu$^{27}$) Growth Hormone Releasing Hormone–Gly$^{45}$," *Protein Engineering*, 1: 195–199 (1987).

(List continued on next page.)

*Primary Examiner*—Kenneth R. Horlick
(74) *Attorney, Agent, or Firm*—Foley & Lardner

(57) ABSTRACT

The method of the invention provides for the formation of a recombinant polypeptide which has been modified at the C-terminal end through the use of a transpeptidation process. The method is suitable for modifying recombinant polypeptides of any source including those which may be commercially available, those derived from recombinant single copy or multicopy polypeptide constructs, or those derived from single or multicopy recombinant fusion protein constructs. The transpeptidation reaction involves contacting an endopeptidase enzyme with a recombinant polypeptide to substitute an addition unit, of one or more amino acids, for a leaving unit, linked to a core polypeptide through a cleavage site recognized by the endopeptidase enzyme. Recombinant polypeptides derived from multicopy polypeptide constructs may be cleaved from the multicopy polypeptide at the N-terminal and C-terminal ends and simultaneously under go substitution of the leaving unit by the desired addition unit. The invention utilizes known and newly discovered cleavage recognition sites to effectuate the desired modification products.

16 Claims, No Drawings

OTHER PUBLICATIONS

Gutniak et al. "Antidiabetogenic Effect of Glucagon–Like Peptide–1(7–36) Amide in Normal Subjects and Patients with Diabetes Mellitus," *New Eng. J. Med.*, 326: 1316–1322 (1992).

Henriksen et al. "Peptide Amidation by Chemical Protein Engineering. A Combination of Enzymatic and Photochemical Synthesis," *J. Am. Chem. Soc.*, 114: 1876–1877 (1992).

Johansen "Isolation of Human Carbonic Anhydrase B and C and Apocarbonic Anhydrase by Affinity Chromatography," *Carlsberg Res. Commun.*, 41: 73–80 (1976).

Kempe et al. "Multiple–copy Genes; Production and Modification of Monomerick Peptides from Large Multimeric Fusion Proteins," *Gene.*, 39: 239–245 (1985).

Kempe et al. "Production and Characterization of Growth Hormone Releasing Factor Analogs Through Recombinant DNA and Chemical Techniques," *Biotechnology*, 4: 565–568 (1986).

Mann et al. "Hemostasis and Thrombosis," *Biochemistry of Thrombin*, J.B. Lippicott Company, Chap. 10 (1987).

Marcus et al. "Agarose–Anthranilate Derivatives in the Purification of Anthranilate Phosphoribosyltransferase," *Methods Enzymol.*, 34: 377–385 (1974).

Matsumoto et al. "Sugars Attached to Starch," *Methods Enzymol.*, 34: 329–341 (1974).

Matsuura et al. "Thiamine Pyrophosphate–Agarose and the Purification of a Thiamine–Binding Protein," *Methods Enzymol.*, 34: 304–304 (1974).

Morihara "Using Proteases in Peptide Synthesis," *Trends in Biotechnology*, J.B. Lippincott Co., 5: 164–170 (1987).

Ohsuye et al. "Cloning of CdnA Encoding a New Peptide C–Terminal α–Amidating Enzyme Having A Putative Membrane–Spanning Domain From *Xenopus laevis* Skin," *Biochem. Biophys. Res. Commun.*, 150: 1275 (1988).

Orskov "Glucagon–Like Peptide–1, A New Hormone of the Entero–Insular Axis," *Diabetologia*, 35: 701–711 (1992).

Pierce, et al. "Interaction of Ribulosebisphosphate Carboxylase/Oxygenase with Transition–State Analogues," *Biochem.*, 19: 934–942 (1980).

Schellenberger et al. "Proteinase–Catalyzed Conversion of A Substance P–Precursor Peptide," *Int. J. Peptide Protein Res.*, 39: 472–476 (1992).

Schellenberger et al. "Mapping the S' Subsites of Serine Proteases Using Acyl Transf to Mixtures of Peptide Nucleophiles," *Biochemistry*, 32: 4349–4353 (1993).

Schellenberger et al. "Peptide Production By A Combination of Gene Expression, Chemical Synthesis, and Protease–Catalyzed Conversion," *Int. J. Peptide Protein Res.*, 41: 326–332 (1993).

Scouten "PropyLipoamide Glass," *Methods Enzymol.*, 34: 288–294 (1974).

Shen et al. "Multiple Joined Genes Prevent Product Degradation in *Escherichia coli,*" *Proc. Natl. Acad. Sci.* USA, 81: 4627–4631 (1984).

Sutton et al. "Phenyl–n–Butylborinic Acid is a Potent Transition State Analog Inhibitor of Lipolytic Enzymes," *BBRC*, 134: 386–392 (1986).

Suzuki et al. "Comparison of the Effects of Various C–Terminal and N–Terminal Fragment Peptides of Glucagon–Like Peptide–1 on Insulin and Glucagon Release From the Isolated Perfused Rat Pancreas," *Endocrinology*, 125: 3109–3114 (1989).

Taylor, et al. "Kinetics of Complex Formation between Human Carbonic Anhydrases and Aromatic Sulfonamides," *Biochemistry*, 9: 2638–2645 (1970).

Thorens et al. "Glucagon–Like Peptide–I and the Control of Insulin Secretion on the Normal State and in NIDDM," *Diabetes*, 42: 1219–1225 (1993).

Williams et al. "The Inhibition of Dihydrofolate Reductase by Folate Analogues: Structural Requirements for Slow–and Tight–Binding Inhibition," *Biochemical Pharm.*, 29: 589–595 (1980).

Kirshner et al. "Gene synthesis,*E. coli* Expression and Purification of The Bovine Growth Hormone Releasing Factor Analog, (Leu$^{27}$, Hse$^{45}$) bGRF", *J. Biotechnology*, 12:247–260 (1989).

* cited by examiner

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 30 amino acids
      (B) TYPE: amino acid
      (D) TOPOLOGY: linear (ii) MOLECULE TYPE: peptide (vii) IMMEDIATE SOURCE:
      (B) CLONE: GLP1 7-36-NH2  (Glucagon-like Peptide)

(xi) SEQUENCE DESCRIPTION: SEQ ID NO: 1:

```
His Ala Glu Gly Thr Phe Thr Ser Asp Val Ser Ser Tyr Leu Glu Gly
 1               5                   10                  15

Gln Ala Ala Lys Glu Phe Ile Ala Trp Leu Val Lys Gly Arg
             20                  25                  30
```

(2) INFORMATION FOR SEQ ID NO: 2:

(i) SEQUENCE CHARACTERISTICS:
      (A) LENGTH: 31 amino acids
      (B) TYPE: amino acid
      (D) TOPOLOGY: linear (ii) MOLECULE TYPE: peptide (vii) IMMEDIATE SOURCE:
      (B) CLONE: GLP1(7-34)-Ala-Phe-Ala (xi) SEQUENCE DESCRIPTION: SEQ ID NO: 2:

```
His Ala Glu Gly Thr Phe Thr Ser Asp Val Ser Ser Tyr Leu Glu Gly
 1               5                   10                  15

Gln Ala Ala Lys Glu Phe Ile Ala Trp Leu Val Lys Ala Phe Ala
```

20 25 30

(2) INFORMATION FOR SEQ ID NO: 3:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (vii) IMMEDIATE SOURCE:
        (B) CLONE: GLP1 (7-36)-Gly (xi) SEQUENCE DESCRIPTION: SEQ ID NO: 3:

His Ala Glu Gly Thr Phe Thr Ser Asp Val Ser Ser Tyr Leu Glu Gly
1          5               10             15

Gln Ala Ala Lys Glu Phe Ile Ala Trp Leu Val Lys Gly Arg Gly
        20            25           30

(2) INFORMATION FOR SEQ ID NO: 4:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (vii) IMMEDIATE SOURCE:
        (B) CLONE: GLP1 (7-34)

(xi) SEQUENCE DESCRIPTION: SEQ ID NO: 4:

His Ala Glu Gly Thr Phe Thr Ser Asp Val Ser Ser Tyr Leu Glu Gly
1          5               10             15

Gln Ala Ala Lys Glu Phe Ile Ala Trp Leu Val Lys
        20            25

(2) INFORMATION FOR SEQ ID NO: 5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 5:

His Asp Glu Phe Glu Arg His
1          5

(2) INFORMATION FOR SEQ ID NO: 6:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (vii) IMMEDIATE SOURCE:
        (B) CLONE: GLP1 (1-34)

(xi) SEQUENCE DESCRIPTION: SEQ ID NO: 6:

His Asp Glu Phe Glu Arg His Ala Glu Gly Thr Phe Thr Ser Asp Val
1          5               10             15

Ser Ser Tyr Leu Glu Gly Gln Ala Ala Lys Glu Phe Ile Ala Trp Leu
        20            25           30

Val Lys (2) INFORMATION FOR SEQ ID NO: 7:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (vii) IMMEDIATE SOURCE:
        (B) CLONE: GRF (1-41) (Growth Hormone Releasing Factor)

(xi) SEQUENCE DESCRIPTION: SEQ ID NO: 7:

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
            20                  25                  30

Glu Ser Asn Gln Glu Arg Gly Ala Arg
        35                  40

(2) INFORMATION FOR SEQ ID NO: 8:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 8:

Ala Arg Leu Gly
 1

(2) INFORMATION FOR SEQ ID NO: 9:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 9:

Asn Gly Pro Arg
 1

(2) INFORMATION FOR SEQ ID NO: 10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Enterokinase cleavage enzyme (xi) SEQUENCE DESCRIPTION: SEQ ID NO: 10:

GACGACGACG ATAAA                                              15

(2) INFORMATION FOR SEQ ID NO: 11:

(i) SEQUENCE CHARACTERISTICS:

(A) LENGTH: 12 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: Factor Xa cleavage enzyme (xi) SEQUENCE DESCRIPTION: SEQ ID NO: 11:

ATTGAAGGAA GA                                                    12

(2) INFORMATION FOR SEQ ID NO: 12:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: Thrombin cleavage enzyme (xi) SEQUENCE DESCRIPTION: SEQ ID NO: 12:

AGAGGACCAA GA                                                    12

(2) INFORMATION FOR SEQ ID NO: 13:

(i) SEQUENCE CHARACTERISTICS:
         (A) LENGTH: 9 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: Ubiquitin cleaving enzyme (xi) SEQUENCE DESCRIPTION: SEQ ID NO: 13:

AGAGGAGGA                                                         9

(2) INFORMATION FOR SEQ ID NO: 14:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: Renin cleavage enzyme (xi) SEQUENCE DESCRIPTION: SEQ ID NO: 14:

CATCCTTTTC ATCTGCTGGT TTAT                                       24

(2) INFORMATION FOR SEQ ID NO: 15:

(i) SEQUENCE CHARACTERISTICS:
         (A) LENGTH: 36 amino acids
         (B) TYPE: amino acid
         (D) TOPOLOGY: linear (ii) MOLECULE TYPE: peptide (vii) IMMEDIATE SOURCE:

(B) CLONE: GLP1 (1-36)

(xi) SEQUENCE DESCRIPTION: SEQ ID NO: 15:

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
                20                  25                  30

Val Lys Gly Arg
            35

(2) INFORMATION FOR SEQ ID NO: 16:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (vii) IMMEDIATE SOURCE:
        (B) CLONE: GRF (1-44)

(xi) SEQUENCE DESCRIPTION: SEQ ID NO: 16:

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
                20                  25                  30

Glu Ser Asn Gln Glu Arg Gly Ala Arg Ala Arg Leu
            35                  40

(2) INFORMATION FOR SEQ ID NO: 17:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (vii) IMMEDIATE SOURCE:
        (B) CLONE: GRF (1-41)-Ala-Arg-Leu-Ala (xi) SEQUENCE DESCRIPTION: SEQ ID NO: 17:

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
                20                  25                  30

Glu Ser Asn Gln Glu Arg Gly Ala Arg Ala Arg Leu Ala
            35                  40                  45

(2) INFORMATION FOR SEQ ID NO: 18:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (xi) SEQUENCE DESCRIPTION: SEQ ID NO: 18:

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa
                20                  25

(2) INFORMATION FOR SEQ ID NO: 19:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (vii) IMMEDIATE SOURCE:
        (B) CLONE: GLP1 (1-37)

(xi) SEQUENCE DESCRIPTION: SEQ ID NO: 19:

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

(2) INFORMATION FOR SEQ ID NO: 20:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 20:

Ala Arg Leu Ala
1

(2) INFORMATION FOR SEQ ID NO: 21:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (vii) IMMEDIATE SOURCE:
        (B) CLONE: GRF (1-44)-Gly (xi) SEQUENCE DESCRIPTION: SEQ ID NO: 21:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu Gly
        35                  40                  45

(2) INFORMATION FOR SEQ ID NO: 22:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 22:

Arg Ala Arg Leu Ala
1               5

```
(2) INFORMATION FOR SEQ ID NO: 23:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (vii) IMMEDIATE SOURCE:
        (B) CLONE: GLP1 (1-34)-Ala-Phe-Ala (xi) SEQUENCE DESCRIPTION: SEQ ID NO: 23:

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Ala Phe Ala
        35

(2) INFORMATION FOR SEQ ID NO: 24:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (vii) IMMEDIATE SOURCE:
        (B) CLONE: GRF (1-41)-Ala (xi) SEQUENCE DESCRIPTION: SEQ ID NO: 24:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala
        35                  40

(2) INFORMATION FOR SEQ ID NO: 25:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (vii) IMMEDIATE SOURCE:
        (B) CLONE: GRF (1-41)-Ala-Arg-Leu (xi) SEQUENCE DESCRIPTION: SEQ ID NO: 25:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

(2) INFORMATION FOR SEQ ID NO: 26:

(i) SEQUENCE CHARACTERISTICS:
        (A) LENGTH: 45 amino acids
        (B) TYPE: amino acid
        (D) TOPOLOGY: linear
```

```
           -continued (ii) MOLECULE TYPE: peptide (vii) IMMEDIATE SOURCE:
         (B) CLONE: GRF (1-41) Ala-Arg-Leu-Gly (xi) SEQUENCE DESCRIPTION: SEQ ID NO: 26:

Tyr Ala Asp Ala Ile Phe Thr Asn Ser Tyr Arg Lys Val Leu Gly Gln
1               5                  10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu Gly
            35                  40                  45
```

ENZYMATIC METHOD FOR MODIFICATION OF RECOMBINANT POLYPEPTIDES

This application is a Continuation of application Ser. No. 08/967,374, filed Nov. 7, 1997, now U.S. Pat. No. 6,037,143, which is a Continuation of application Ser. No. 08/520,485 filed Aug. 29, 1995 (abandoned), which is a Divisional of application Ser. No. 08/470,220 filed Jun. 6, 1995, now U.S. Pat. No. 5,507,826, and application Ser. No. 08/095,162, filed Jul. 20, 1993, now U.S. Pat. No. 5,512,459.

BACKGROUND OF THE INVENTION

Many naturally occurring proteins and peptides have been produced by recombinant DNA techniques. Recombinant DNA techniques have made possible the selection, amplification and manipulation of expression of the proteins and peptides. For example, changes in the sequence of the recombinantly produced proteins or peptides can be accomplished by altering the DNA sequence by techniques like site-directed or deletion mutagenesis.

However, some modifications to a recombinantly produced protein or peptide cannot be accomplished by altering the DNA sequence. For example, the C-terminal α-carboxyl group in many naturally occurring protein and peptides often exists as an amide, but this amide typically is not produced through recombinant expression and is biologically converted after expression in vivo from a precursor protein to the amide.

A method of forming a C-terminal amide on a recombinantly produced polypeptide by the action of an enzyme is known. The enzyme is peptidyl glycine α-amidating monooxygenase and is present in eukaryotic systems. The enzyme has been used to form an amide on the C-terminal amino acid of recombinantly produced peptides, like human growth hormone releasing hormone in vitro, as described by J. Engels, *Protein Engineering*, 1:195–199 (1987). While effective, the enzymatic method is time consuming, expensive, given unpredictable yields, and requires significant post-reaction purification. The enzymatic method is also limited to modifying the recombinantly produced peptide by C-terminal amidation.

Accordingly, there is a need for a chemical method that provides for modification of C-terminal α-carboxyl groups of a recombinantly produced polypeptide. There is also a need for a method of modification that allows addition of a variety of moieties to the C-terminal α-carbon reactive groups of a recombinantly produced polypeptide and that is convenient, cheap and capable of producing terminally modified recombinant polypeptides in high yield. Therefore, it is an object of the invention to develop a biochemical method for selective modification of the C-terminal amino acid of a recombinantly produced polypeptide. A further object is to provide a simple and economic method for modification of the C-terminal amino acid through a transpeptidation reaction.

SUMMARY OF THE INVENTION

These and other objects are accomplished by the present invention. The present invention is an economical biochemical method for modification of the C-terminal amino acid of recombinant polypeptides to provide polypeptides which cannot normally be obtained through recombinant technology.

The process of the invention utilizes transpeptidation which involves contacting an endopeptidase enzyme, specific for an enzyme cleavage site, with a recombinant polypeptide, composed of at least one core linked by a cleavage site to a leaving unit, in the presence of an addition unit. The endopeptidase enzyme cleaves the leaving unit from the core at the cleavage site and simultaneously causes the core and the addition unit to form the desired modified recombinant polypeptide. Alternatively, the cleavage of the leaving unit and the formation of the linkage between the core and addition unit may be completed in two separate steps. Subsequent to transpeptidation, further enzymatic modification of the terminal amino acid carboxy group of, the addition unit, through known enzymatic methodology, is possible.

The endopeptidase enzymes used according to the method of the invention include those of the serine or cysteine peptidase class. The endopeptidase enzymes trypsin and thrombin, of the serine peptidase class, are especially desirable endopeptidase enzymes to serve as cleavage enzymes for the method of the invention.

The recombinant polypeptide starting material includes a core which may be a truncated version of its natural form. The core may be truncated through deletion of amino acids at either, or both, of its C-terminal and N-terminal ends depending on the product desired. The recombinant polypeptide also includes a leaving unit linked to the core by an enzyme cleavage site recognized by the endopeptidase enzyme. The leaving unit may be one or more amino acid residues.

The amino acid cleavage site for the endopeptidase enzyme may be recognized by the endopeptidase enzyme in solo or as a part of a multiple amino acid recognition sequence. In addition, according to the method of the invention, cleavage sites which are normally cleaved by an endopeptidase enzyme may be rendered less reactive or unrecognizable when adjacent to certain other amino acids. Use of this knowledge to cause some cleavage sites to be less reactive is used advantageously to render new and substantial utility to endopeptidase enzymes which may otherwise be precluded from use in certain transpeptidation reactions. The ability to cause combination of the addition unit with the core is a desirable characteristic of the endopeptidase enzyme. The addition unit may be one or more amino acid residues which may be modified at the C-terminal α-carboxy at the time of transpeptidation, or may be further treated by known enzymatic methodologies subsequent to transpeptidation.

The entire transpeptidation process may be done in a single step under very mild conditions. The starting polypeptide of the invention may be a single-copy recombinant polypeptide, a multi-copy recombinant polypeptide or a single or multi-copy recombinant fusion protein construct. The number and sequence of steps of cleaving and reacting the starting material can vary depending on the starting material used.

The recombinant multicopy polypeptide may be multiple copies of the single copy polypeptide linked together with or without intraconnecting peptides. If an intraconnecting peptide is present, it has at least one site that is selectively cleavable by the endopeptidase cleavage enzyme. The intraconnecting peptide may also serve as the leaving group from the C-terminal end of a single copy core polypeptide.

The single copy polypeptides within a multicopy polypeptide may be linked directly to each other through an amino acid linkage recognized by the endopeptidase cleavage enzyme. According to this method of the invention, it is preferred that a multicopy recombinant polypeptide is cleaved into single copy core units and simultaneously transpeptidated when in the presence of a suitable addition unit. The downstream core acts as a leaving group for the core immediately preceding it. The terminal single copy core of a multicopy recombinant polypeptide is linked to a suitable leaving unit so that all single-copy polypeptides within the multicopy recombinant polypeptide are transpeptidated according to the method of the invention.

A fusion protein construct has three tandomly-linked segments including a binding protein connected via an interconnecting peptide to a single copy or multicopy polypeptide. The interconnecting peptide has at least one site that is selectively cleavable by a chemical or enzymatic method. The binding protein with the interconnecting peptide acts as a biological protecting group and aids in the purification of the recombinant multicopy polypeptide.

DETAILED DESCRIPTION OF THE INVENTION

Recombinant DNA techniques have made possible the selection, amplification, and manipulation of expression of many naturally occurring proteins and peptides. It is often desirable to selectively modify a recombinant polypeptide at the N-terminal α-amine and/or C-terminal α-carboxyl groups. For example, the C-terminal reactive carboxyl groups in some naturally occurring proteins and peptides can be selectively converted to an amide to provide for enhancement of biological activity. Alternatively, a D-amino acid or peptide could be added to replace a terminal amino acid.

These modifications can result in the formation of analogs of the recombinantly produced polypeptide that are longer acting and more potent than the naturally occurring polypeptide. Generally, these types of modifications to the recombinantly produced polypeptide are not accomplished by alteration of the DNA sequence for the recombinantly produced polypeptide because there is no genetic code providing for amino acid amides, or incorporation of D-amino acid or an amino acid derivative.

The present invention provides a process for the selective modification of a recombinantly produced polypeptide by a single-step transpeptidation process at cleavage sites specific for various cleavage enzymes. Alternatively, a two-step transpeptidation process may be used whereby the polypeptide is first enzymatically cleaved at the cleavage site to form the hydrolysis product, which is then condensed with a suitable addition unit to form the modified recombinant polypeptide product.

The process allows for efficient modification of recombinant polypeptides to produce products for which there is no genetic code, for example, C-terminal α-carboxyl amidation.

PROCESS

The process provides for modification of a recombinant polypeptide through transpeptidation. For purposes of this invention, "transpeptidation" is defined as that process whereby a terminal amino acid or a chain of amino acids (leaving unit), linked through an endopeptidase enzyme cleavage site at the C-terminal end of a recombinant polypeptide, is replaced by another amino acid or chain of amino acids (addition unit), in the presence of an endopeptidase cleavage enzyme. The method of the invention utilizes an endopeptidase enzyme, preferably of the serine or cysteine class, as the cleavage enzyme to catalyze the transpeptidation process.

The recombinant polypeptide includes a core portion and a leaving unit. The core is any useful polypeptide sequence such as a native sequence, a modified native sequence, a non-native sequence having biological activity, transacted forms thereof and similar versions. The leaving unit is one or more amino acid units. Preferably, the leaving unit is linked to the core through an amino acid linkage which is recognized as a cleavage site by the endopeptidase cleavage enzyme. According to the method of the invention, the core polypeptide linked to a leaving unit may be derived from any source including chemical synthesis, recombinant single copy polypeptide expression, multicopy polypeptide expression, or single or multicopy fusion protein constructs.

The recombinant polypeptide is contacted with at least one endopeptidase cleavage enzyme specific for at least one cleavage site. The enzymatic cleavage of the recombinant polypeptide at the linkage of the core portion and the leaving unit is conducted in the presence of an addition unit. An addition unit is a single or multiple amino acid residue which may be modified at its C-terminal α-carbon. Alternatively, modification of the C-terminal α-carbon end of the addition unit may be done subsequent to the transpeptidation process.

The method of the invention also provides for cleavage of recombinant multicopy polypeptides into single copy polypeptides by the endopeptidase cleavage enzyme. Under the method of the invention, in the presence of a suitable leaving unit, cleavage of the multicopy polypeptide will occur simultaneously with single-step transpeptidation. Alternatively, the polypeptide may be cleaved, at the cleavage site, to form the hydrolyzed cleaved polypeptide which subsequently undergoes condensation with the addition unit to form the modified recombinant polypeptide product.

I. Transpeptidation

The method of the invention provides a modified recombinant polypeptide product produced by transpeptidation of a recombinant polypeptide. The sequence and number of steps in the method of the invention can be varied depending upon the desired modification of the recombinant polypeptide, the amino acid sequence of the desired product peptide, and the starting material selected. The transpeptidation method of the invention calls for the recombinant polypeptide to be contacted with an endopeptidase cleavage enzyme, which has specific cleavage activity at the linkage between the core and the leaving unit.

The endopeptidase cleavage enzyme cleaves the leaving unit from the carboxy terminal of the core of the recombinant polypeptide. Although it is not intended to be a limitation of the invention, it is believed that during this cleavage, the enzyme forms an acyl- or thioacyl-enzyme intermediate with the core. In the presence of an appropriate addition unit, under proper conditions, the enzyme causes the addition unit to add to the cleaved core. Although it is not intended to be a limitation of the invention, it is believed that to accomplish this combination, the addition unit displaces the cleavage enzyme from the acyl-enzyme intermediate and links to the core polypeptide where the leaving unit was linked. The production of the modified recombinant polypeptide is monitored by HPLC or other analytic procedure and the reaction is stopped by the addition of an acidic solution when the reaction has reached completion. The amino acid or terminal amino acid residue of the addition unit may already be modified at its carboxy terminal end at the time of undergoing the transpeptidation reaction, such as by modification of the C-terminus carboxylic acid to a carboxamide, or, alternatively, be modified after formation of the modified recombinant polypeptide.

According to the method of the invention, preferably, the cleavage site recognized by the cleavage enzyme is a site not duplicated in the core or is not at an enzyme accessible site within the core. The method of the invention is also directed to an endopeptidase enzyme cleavage of a multicopy recombinant polypeptide into single copy recombinant polypeptides and simultaneously transpeptidating the cores to form the modified recombinant polypeptide in a single biochemical reaction.

The invention is further directed to modified enzyme cleavage sites which, when adjacent to certain amino acid residues, render the site unrecognizable or less reactive to cleavage. The discovery of the use of these unrecognizable or less reactive sites to prevent cleavage, renders new and substantial utility to various cleavage enzymes which would otherwise be precluded from use in certain transpeptidation reactions due to the detrimental effect of cleavage of recombinant polypeptides at sites within the desired core.

The leaving units to be cleaved from the core are specifically chosen to provide a suitable leaving unit for the specific endopeptidase cleavage enzyme. The addition units are chosen to provide the amino acid or peptide chain to complete formation of the desired modified recombinant polypeptide. The amino acid or terminal amino acid of the addition unit may be modified at the C-terminal α-carboxy or it may be modified after transpeptidation. Alternatively, the addition unit may be a peptidomimetic and serve as a linker between the core and attached functional unit, as disclosed in patent application Ser. No. 08/094,819 abandoned.

The cleavage enzymes, according to the method of the invention, include the class of endopeptidases. The endopeptidases suitable for use in the present invention include the serine and cysteine peptidases. Although it is not intended to be a limitation of the invention, the mechanism of action of serine and cysteine endopeptidases is believed to involve the formation of an acyl- or thioacyl-enzyme intermediate with the core after cleaving the leaving unit. Under appropriate reaction conditions, it is believed that the addition unit acts as a neucleophile and displaces the endopeptidase cleavage enzyme from the acyl- or thioacyl- enzyme intermediate.

Serine peptidases are in a group of animal, plant and bacteria endopeptidases which have a catalytically active serine residue in their active center. Representatives examples of endopeptidases of the serine peptidase classification include trypsin, thrombin, chymotrypsin, enterokinase, subtiliisin, and factor Xa. Representative examples of the scysteine peptidase classification include ficin and papian.

The endopeptidase trypsin is found in the pancreas of all vertebrates. It is released via the pancreatic duct into the duodenum as trypsinogen. Conversion of trypsinogen into trypsin is initiated in the small intestine by enterokinase. Natural or synthetic forms of trypsin are suitable for the method of the invention.

Trypsin is known for its pronounced cleavage site specificity, catalyzing hydrolysis of only the carboxyl end of the -Lys-X and -Arg-X bonds. Trypsin's affinity for cleavage at the -Lys-X bond is significantly diminished when immediately adjacent to an amino acid containing a carboxylic acid side chain, specifically including the amino acids glutamic acid and aspartic acid (i.e., X=glutamic or aspartic acid). A discovery of the present invention utilizes the knowledge of decreased cleavage activity at the -Lys-X cleavage sites when X=an amino acid containing adjacent to an amino acid containing a carboxylic acid side chain (i.e., X=glutamic or aspartic acid). This discovery has rendered the endopeptidase trypsin of great utility in the formation of modified recombinant polypeptides, according to the method of the invention. Natural or synthetic forms of thrombin are suitable for the method of the invention.

The glycoprotein endopeptidase thrombin, also of the serine peptidase classification, is responsible for the conversion of fibrinogen to fibrin. It is naturally produced during blood coagulation by the action of factor $X_a$ upon prothrombin. This endopeptidase has considerable sequence homology with trypsin and contains the catalytically important residues His, Asp, and Ser in the B chain. Thrombin has a cleavage specificity for the carboxy end of the -Arg- cleavage site in specific peptide sequences known as recognition sequences.

Thrombin is known for its cleavage site specificity at the carboxyl side of the Arg- residue within the known recognition sequence for the cleavage site -Arg is Gly-Pro-Arg-. A discovery of the present invention is that thrombin also cleaves at the carboxyl side of Arg- within the recognition sequence of Gly-Ala-Arg. This discovery enhances the use of thrombin for transpeptidation by the method of this invention as well as other synthetic reactions where knowledge of the Gly-Ala-Arg recognition sequence will be of benefit.

A. Transpeptidation Using the Endopeptidase Trypsin

The transpeptidation process according to the method of the invention may be accomplished using starting recombinant polypeptide derived from single or multicopy constructs, or single or multicopy fusion protein constructs.

1. Trypsin Transpeptidation of a Single Copy Recombinant Polypeptide

The following description is based upon a particular recombinantly-derived core starting polypeptide, however, it is understood that the method of the invention is suitable for transpeptidation of polypeptides, regardless of the source.

The transpeptidation process of the invention is preferably a one-step reaction conducted in a buffer solution capable of maintaining pH at about pH 2–13, preferably pH 3–12, and more preferably pH 5–11. Suitable buffers for the present invention include Tris, succinate, citrate, phosphatate, acetate, tricine, hepes, and the like. In one embodiment of the invention using the serine endopeptidase trypsin as the cleavage enzyme for the transpeptidation method of the invention, the modified recombinant polypeptide, for example Glucagon-like Peptide 1 (GLP1) (7–36)-NH$_2$ (SEQ ID NO: 1), is produced. The product GLP1 (7–36)-NH$_2$ (SEQ ID NO: 1) is produced in several tissues and has been shown to be an incretin, and is commonly referred to as GLIP. The sequence of GLP1 (7–36)-NH$_2$ (SEQ ID NO:1) is:

```
-His-Ala-Glu-Gly-Thr-Phe-Thr-Ser-
  7

Asp-Val-Ser-Ser-Tyr-Leu-Glu-Gly-Gln-

Ala-Ala-Lys-Glu-Phe-Ile-Ala-Trp-Leu-
      26  27

Val-Lys-Gly-Arg-NH₂
     34      36
```

According to the invention, the trypsin catalyzed transpeptidation reaction, causing substitution of the addition unit for the leaving unit, is in competition with the trypsin catalyzed hydrolysis at the carboxy terminus of the amino acid at the cleavage site. There are two ways to affect the reaction mixture to favor the transpeptidation process. In the first, the reaction is conducted in an aqueous buffer solution with reactant concentrations conducive to the transpeptidation process. Alternatively, organic solvents may be used to favor the transpeptidation process over hydrolysis.

In the first variation, the recombinant polypeptide GLP1 (7–34) core linked to the leaving unit -Ala-Phe-Ala at a -Lys- cleavage site (SEQ ID NO:2):

```
-His-Ala-Glu-Gly-Thr-Phe-Thr-Ser-
  7

Asp-Val-Ser-Ser-Tyr-Leu-Glu-Gly-Gln-

Ala-Ala-Lys-Glu-Phe-Ile-Ala-Trp-Leu-
       26   27

Val-Lys-Ala-Phe-Ala
      34
``` is dissolved in buffer. To the transpeptidation mixture is added the suitable addition unit, containing desired amino acid or peptide sequence. The amount of addition unit required is dependent on the dissociation constant (KM) of the endopeptidase-acyl intermediate to the recombinant polypeptide and the concentration of recombinant polypeptide in the mixture. Typically, the amount of addition unit is about one equivalent to 20 times the $K_M$ of the addition unit to the acyl-enzyme intermediate, preferably 10×$K_M$ of the addition unit to the acyl-enzyme intermediate. For example, Gly-Arg-NH$_2$ or Gly-Arg-Gly are desired sequences which are suitable addition units for synthesis of the modified recombinant polypeptide product GLIP (SEQ ID NO: 1) and GLP1 (7–36) -Gly (SEQ ID NO:3),

```
-His-Ala-Glu-Gly-Thr-Phe-Thr-Ser-
  7

Asp-Val-Ser-Ser-Tyr-Leu-Glu-Gly-Gln

Ala-Ala-Lys-Glu-Phe-Ile-Ala-Trp-Leu
       26   27

Val-Lys-Gly-Arg-Gly
      34        36
``` respectively. The cleavage enzyme trypsin is added in an effective catalytic amount but not so great as to cause substantial secondary reactions such as cleavage at other sites, hydrolysis, and the like. The cleavage enzyme trypsin is added to the reaction mixture in a trypsin:polypeptide molar ratio of about 1:10 to 1:500,000, preferably 1:100 to 1:100,000, and more preferably 1:200 to 1:50,000.

The production of the modified recombinant polypeptide product GLP (SEQ ID NO: 19) or GLP1 (7–36) -Gly (SEQ ID NO: 3) is monitored by HPLC, laser desorption, mass spectrometry, or other analytical method, and the reaction stopped by the addition of an acid solution. The reaction procedure may be stopped by an acid solution at about pH 3. Suitable acid solutions for stopping the reaction include hydrochloric, sulfuric, acetic, and the like.

Alternatively, the trypsin catalyzed competitive reactions of hydrolysis and transpeptidation may be shifted in favor of transpeptidation through the use of organic solvents. Suitable solvents for the transpeptidation reaction, according to the method of the invention, include DMSO and 75% v:v, N,N-dimethylacetamide and 95% v:v. Bongers et al., *Int. J. Peptide Protein Res.*, 40:268 (1992).

If the desired modified recombinant polypeptide product requires an amidated C-terminal amino acid but an addition unit including a non-amidated terminal amino acid was used, the C-terminal α-carboxyl group may be amidated in a further step. The C-terminal α-carboxyl group may be amidated as described by Bongers et al., cited supra. for the GLP1 (7–36)-Gly (SEQ ID NO: 3) by the use of the C-terminal α-carboxyl amidating enzyme, as described in Henriksen et al., *J. Am. Chem. Soc.*, 114:1876–1877 (1992); and Ohsuye et al., *Biochem. Biophys. Res. Commun.*, 150:1275 (1988). The foregoing references describe the procedure and are incorporated herein by reference.

The modified recombinant polypeptide product is purified from the mixture by HPLC, ion exchange chromatography, hydrophobic interaction chromatography, or particular exclusion chromatography. To further reduce contamination, the separated product may be further purified by sequential use of the aforementioned methods. The recombinant polypeptide product may be used immediately or may be stored by lypholization and cryopreservation at about −70° C.

In this variation, the endopeptidase cleavage enzyme trypsin cleaved the truncated GLPI core from the leaving unit at the 34–35 Lys-Ala cleavage site. (See SEQ ID NO:2). As stated earlier, trypsin is known for its cleavage site specificity at -Lys-X and -Arg-X bonds. It is noted that the GLP1 (7–34) (SEQ ID NO: 4) core also contains the trypsin cleavage site -Lys- at the 26–27 amino acid position. This lysyl was not cleaved by trypsin. It is believed that the adjacent carboxylic acid side chain containing amino acid adjacent to -Lys- rendered the -Lys-cleavage site less reactive. The method of the invention utilizes the knowledge that -Lys- followed by an amino acid with a carboxylic acid containing side chain is a poor substrate, and the discovery that lysyl glutamyl at 27–28 is not hydrolyzed during the time required for complete hydrolysis of lysl-histidyl at 6–7 and lysl-glysyl at 34–35 of GLP1 (1–37) (SEQ ID NO: 19). For example, -Glu- renders lysyl poor cleavage site in -Lys-Glu- a poor substrate for trypsin. This allows the serine peptidase trypsin to be utilized as a cleavage enzyme when there exists multiple recognized -Lys- cleavage sites, but only the desired cleavage site is not adjacent to an amino acid containing a carboxyl group containing side chain.

2. Trypsin Transpeptidation of a Single Copy Recombinant Polypeptide Derived From a Fusion Protein Construct The GLP1 (SEQ ID NO: 19) and GLP1 (7–36)-Gly (SEQ ID NO: 3) modified recombinant product polypeptides may be produced by the method of the invention starting with a recombinant polypeptide derived from a recombinant single copy fusion protein starting product. As discussed infra, a fusion protein construct serves as a carrier protein system for recombinant polypeptides and provides an efficient system for chromatographic purification. In this variation, the fusion protein construct is first purified from the other cell constituents, as described below at section II. (See this section also for definitions of the fusion protein terms.) Once the fusion protein construct is purified from the other cell constituents, preferably, the binding protein is separated from the recombinant single copy polypeptide. According to the method of the invention, the separation of the binding protein from the recombinant single copy polypeptide is accomplished by cleavage of the interconnecting polypeptide or amino acid. Depending on the interconnecting polypeptide or amino acid used, cleavage may be accomplished by the use of a cleavage enzyme or chemical cleavage reagent. For example, the chemical cleavage agent cyanogenbromide (CNBr) in 70% formic acid cleaves the interconnecting amino acid methionine. Once the single copy polypeptide is released from the binding protein, it is separated from the binding protein by known methods in the art such as precipitation and chromatographic procedures including size exclusion, ion exchange, HPLC, and the like. Once purified, the GLP1 (7–34)-Ala-Phe-Ala (SEQ ID NO: 2) is transpeptidated according to the method of the invention, as described above.

3. Trypsin Transpeptidation of a Multicopy Recombinant Polypeptide

In a third variation, according to the method of the invention, a recombinant multicopy polypeptide is cleaved into recombinant single copy polypeptides simultaneous with the transpeptidation process. The number of single copy polypeptides which may be incorporated into a recombinant multicopy polypeptide is limited only by the physical capabilities of the specific expression system selected for expression of the recombinant multicopy polypeptide. The recombinant multicopy polypeptide may include multiple single copy core polypeptides with intraconnecting peptides between individual single copy core polypeptides, or the single copy core polypeptides may be linked directly to one another. In either alternative, the linkage between the intraconnecting polypeptide and core, or between directly linked individual cores, is preferably a cleavage site recognized by the endopeptidase cleavage enzyme. Further, in either variation of a multicopy polypeptide, only the terminal single copy polypeptide need be linked to a leaving unit. In the non-terminal single copy recombinant polypeptides, the downstream polypeptide acts as a leaving group for the immediately preceding polypeptide.

According to the method of the invention, when the recombinant multicopy polypeptide is composed of single copy core polypeptides linked by intraconnecting peptide, the potential peptides which may be used as intraconnecting peptides only require that the terminal ends are composed of amino acids which will not inhibit the cleavage activity of the endopeptidase cleavage enzyme at the linkage. For example, in one variation, the 1–6 amino acid sequence of the unprocessed natural form of GLP1 may serve as an intraconnecting polypeptide between individual single copy GLP1 (7–34) unit (SEQ ID NO:4):

```
His-Asp-Giu-Phe-Giu-Arg-His-Ala
1                             7

Glu-Gly-Thr-Phe-Thr-Ser-Asp-Vai-Ser

Ser-Tyr-Leu-Glu-Gly-Gln-Ala-Ala

Lys-Glu-Phe-Ile-Aia-Trp-Leu
26  27

Val-Lys
34
```

In this embodiment, trypsin will cleave the recombinant multicopy polypeptide into recombinant single copy polypeptides at the -Arg- residue at amino acids 6–7 and at the -Lys- residue at amino acid 34 to yield single copies of core GLP1 (7–34) (SEQ ID NO: 4) and intraconnecting units of (SEQ ID NO:5):

```
His-Asp-Glu-Phe-Glu-Arg-His
1                   6   7
```

The reaction will also yield a single terminal Ala-Phe-Ala leaving group. When the reaction is conducted in the presence of an appropriate nucleophilic addition unit, such as Gly-Arg-NH$_2$ or Gly-Arg-Gly, transpeptidation occurs yielding the modified recombinant polypeptide products GLP1 (SEQ ID NO: 19) and GLP1 (7–36) -Gly (SEQ ID NO: 3), respectively.

It is further recognized that the interconnecting polypeptides may be cleaved before or after transpeptidation by a chemical or enzymatic cleavage agent. (See Table 2.)

According to the method of the invention, the recombinant multicopy polypeptide is purified as described in Scopes et al., *Protein Purification: Principles and Practice*, Springer-Verlag, New York (1987), which is incorporated herein by reference. The purified multicopy recombinant polypeptide is then further processed according to the method of invention. As previously discussed for the recombinant single polypeptide, the reaction is conducted, preferably, in a buffered solution at pH 5–11. As described earlier, the amount of addition unit requires is the range of one equivalent up to $20 \times K_M$ of the enzyme to the addition unit. Trypsin is added in a trypsin:polypeptide ratio of preferably about 1:2000 to 1:50,000. Simultaneous cleavage of the recombinant multicopy polypeptide and transpeptidation yields multiple copies of SEQ. ID NO:5, multiple copies of recombinant GLP1 (7–34) (SEQ ID NO: 4) core, and one Ala-Phe-Ala leaving group. The Gly-Arg-NH$_2$ or Gly-Arg-Gly addition units act as a nucleophile and transpeptidation occurs at amino acid residue 34. The production of modified recombinant polypeptide GLP1 (SEQ ID NO: 19) or GLP1 (7–36)-Gly (SEQ ID NO: 3) product is monitored by HPLC or other analytical technique and the reaction stopped by the addition of a suitable acid as described above.

In an alternative variation, the modified recombinant polypeptide products may be formed, by the method of the invention, through simultaneous cleavage and transpeptidation of recombinant multicopy polypeptide units composed of multiple single copy polypeptide units connected without intervening intraconnecting peptides. According to this variation of the invention, for example, a recombinant multicopy polypeptide multiple single copy GLP1 (7–34) (SEQ ID NO: 4) cores with a terminal GLPI (7–34) (SEQ ID NO: 4) core linked to a Ala-Phe-Ala (SEQ ID NO: 2) leaving unit is expressed. The expressed multicopy recombinant polypeptide is purified from cell constituents, as previously described. The multicopy construct is treated with the endopeptidase enzyme trypsin, as previously described by the method of the invention. Trypsin will cleave the multicopy polypeptide into single copy polypeptides at the 34–7 -Lys- residue (see SEQ ID NO:3). Simultaneous with cleavage, the single copy polypeptides will undergo transpeptidation, as previously described, yielding the GLP1 (SEQ ID NO: 19) or GLPI (7–36)-Gly (SEQ ID NO: 3) products in the presence of Gly-Arg-NH$_2$ or Gly-Arg-Gly addition units, respectively.

In another variation, it is further recognized, that the GLP1 (1–36)-NH$_2$ (SEQ ID NO: 15) and GLP1 (1–36)-Gly (SEQ ID NO: 19) modified recombinant product may be prepared, according to the method of the invention, using mutant forms of trypsin. In this variation, a multicopy recombinant polypeptide, as previously described, is synthesized using multiple single cope GLP1 (1–34) units (SEQ ID NO:6)

```
His-Asp-Glu-Phe-Glu-Arg-His-Ala
1                             7

Glu-Gly-Thr-Phe-Thr-Ser-Asp-Val-Ser

Ser-Tyr-Leu-Glu-Gly-Gln-Ala-Ala

Lys-Glu-Phe-Ile-Ala-Trp-Leu
26  27

Val-Lys
34
``` contiguously connected without an intraconnecting peptide and with a leaving group only at the terminal polypeptide. The mutant trypsin endopeptidase enzymes used for this variation have a decreased rate of cleavage at the -Arg- site and a normal rate of cleavage at the -Lys- cleavage site. These mutant forms will, therefore, cleave the recombinant polypeptides at the 34 -Lys- residue, but will not cleave at the -Arg- 6 residue yielding multiple single copy GLP1 (1–36) (SEQ ID NO: 15) and a single leaving group. In the presence of a suitable addition unit such as Gly-Arg-NH$_2$ or Gly-Arg-Gly, under the conditions of the invention, the GLP1 (1–34) (SEQ ID NO: 6) core units will be transpeptidated yielding the GLP1 (1–36)-NH$_2$ (SEQ ID NO: 15) or GLP1-Gly (SEQ ID NO: 19) products.

The foregoing transpeptidation processes described for a multicopy recombinant polypeptide may alternatively be conducted in organic solvents conducive to the transpeptidation process, as described earlier.

4. Trypsin Transpeptidation of a Multicopy Recombinant Polypeptide Derived From a Fusion Protein Construct The modified recombinant polypeptide products may be produced, according to the method of invention, by transpeptidation of recombinant single copy core polypeptides units which have been derived from a multicopy polypeptide unit which has been derived from a fusion protein construct. The number of recombinant single copy core polypeptides included within the recombinant multicopy polypeptide is limited only by the physical capabilities of the chosen expression system.

The multicopy fusion protein construct is formed, purified from the other cell constituents, and the binding protein is separated from the recombinant polypeptide, as described at section II. The purified recombinant multicopy polypeptide, separated from the binding protein, is then further treated as described above to yield the desired modified recombinant polypeptide products.

B. Transpeptidation Using the Endopeptidase Thrombin

Another example of the endopeptidase which may act as a cleavage enzyme according to the method of the invention is thrombin. As described earlier, thrombin has a cleavage site preference at the carboxy end of -Arg-, (Y-Arg-X), within the known recognition sequence Gly-Pro-Arg. A discovery of the present invention is that thrombin also cleaves at the carboxy end of -Arg- (Y-Arg-X) within the cleavage recognition sequence Gly-Pro-Arg. The discovery of this recognition sequence renders the endopeptidase enzyme thrombin new and substantial utility in preparation of modified recombinant polypeptides by the method of this invention and other recombinant methodologies. In the past, the recombinantly produced growth hormone releasing factor (GRF) (1–44)-NH$_2$ (SEQ ID NO: 16) was produced through the use of an α-amidating enzyme. By the method of the present invention, the amidated form of GRF may be synthesized through the use of an appropriate addition unit to a core, or by amidation of an addition unit after transpeptidation by the method of the invention.

1. Thrombin Transpeptidation of a Single Copy Recombinant Polypeptide

The transpeptidation process of the present invention, utilizing the endopeptidase enzyme thrombin, is a one-step reaction. As discussed earlier for trypsin, conditions are maintained to favor the competing reaction of hydrolysis and transpeptidation. Within an aqueous environment, the reaction is conducted in a buffer solution capable of maintaining pH at about pH 2–13, preferably pH 3–12, and more preferably pH 5–11. Suitable buffers for the present invention are as previously described for trypsin. Using the serine endopeptidase thrombin as a cleavage enzyme for cleavage and transpeptidation, the recombinant polypeptide includes a GRF (1–41) (SEQ ID NO: 7) core linked to leaving unit. A known leaving unit is Ala-Arg-Leu-Ala (SEQ ID NO: 20). It is recognized that there are many potential leaving units, including peptides and single amino acids such as -Ala-. The sequence of GRF (1–41) (SEQ ID NO:7) is:

Tyr-Ala-Asp-Ala-Ile-Phe-Thr-Asn-Ser-Tyr-Arg-Lys-
1

Val-Leu-Gly-Gln-Leu-Ser-Ala-Arg-Lys-Leu-Leu-Gln-
13

Asp-Ile-Met-Ser-Arg-Gln-Gln-Glu-Ser-Asn-Gln-
25

Glu-Arg-Gly-Ala-Arg
37           41

A suitable addition unit for synthesis of GRF (1–44) NH$_2$ (SEQ ID NO: 16) is Ala-Arg-Leu-NH$_2$ and for synthesis of GRF (1–44)-Gly (SEQ ID NO: 21), a suitable addition unit is Ala-Arg-Leu-Gly (SEQ ID NO:8). The present variation uses the discovery that thrombin recognizes the cleavage site -Arg- within a Gly-Ala-Arg recognition sequence.

This knowledge is used to cleave the Ala-Arg-Leu-Ala (SEQ ID NO: 20) leaving unit from the core at the -Arg- within Gly-Ala-Arg. To the recombinant polypeptide GRF (1–41) -Ala-Arg-Leu-Ala (SEQ ID NO: 17) is added the addition unit at an amount of about one equivalent to 20 times the K$_M$ of the addition unit to the acyl-enzyme intermediate, preferably 10×K$_M$ of the addition unit to the aceyl-enzyme intermediate. For example, Ala-Arg-Leu-NH$_2$ or Ala-Arg-Leu-Gly (SEQ ID NO:8) are suitable addition units for synthesis of the modified recombinant GRF (1–44) -NH$_2$ (SEQ ID NO: 16) and GRF (1–44)-Gly (SEQ ID NO: 21) products. The cleavage enzyme thrombin is added to the mixture in a thrombin:polypeptide ratio of about 1:10 to 1:500,000, preferably 1:100 to 1:100,000, and more preferably 1:200 to 1:50,000.

The production of GRF (1–44)-NH$_2$ (SEQ ID NO: 16) is monitored by HPLC or other appropriate analytical technique and the reaction stopped by the addition of an enzyme inhibitor such as phenyl methane sulfonyl fluoride (PMSF) or diisopropyl phospyoryl fluoride (DPF). The modified recombinant polypeptide is separated from the reaction mixture by reverse phase chromatography, hydrophobic interation chromatography, ion exchange chromatography, or HPLC. The recombinant polypeptide product may be stored at about -20° C. to about -80° C. after lyopholazation.

Alternatively, the thrombin catalized competitive reactions of hydrolysis and transpeptidation may be shifted in favor of transpeptidation through the use of organic solvents. Suitable solvents for the transpeptidation reaction, according to the method of invention, include DMSO and 75% v:v N,N-dimethylacetamide and 95% v:v. Bongers et al., cited supra.

2. Thrombin Transpeptidation of a Single Copy Recombinant Polypeptide Derived From a Fusion Protein Construct Recombinant GRF (1–44)-NH$_2$ (SEQ ID NO: 16) can be prepared, according to the method of the invention, from a recombinant polypeptide derived from a single copy fusion protein construct. The expression of the single copy fusion protein construct is described infra. In brief, the binding protein of the fusion protein construct will be connected to the single copy recombinant polypeptide through an interconnecting peptide. The interconnecting peptide may be a single amino acid which is cleavable by a chemical cleavage agent or a peptide which terminates with an amino acid sequence recognizable by a cleavage enzyme. For example, the tetrapeptide Asn-Gly-Pro-Arg (SEQ ID NO:9) is a suitable interconnecting peptide for the fusion protein construct containing the GRF (1–41)-Ala-Arg-Leu-Ala (SEQ ID NO: 17) single copy recombinant polypeptide.

Once expressed, the fusion protein construct is purified from other cell constituents, and the single copy recombinant polypeptide is then separated from the binding protein, as described in U.S. patent application Ser. No. 07/552,810, U.S. Pat. No. 5,595,887, the disclosure of which is incorporated herein by reference. For example, a human carbonic anhydrase fusion protein may be separated from the interconnecting peptide of the sequence, Asn-Gly-Pro-Arg (SEQ ID NO:9), through the use of guanidine hydrochloride.

The cleaved single copy recombinant GRF (1–41)-Ala-Arg-Leu-Ala (SEQ ID NO: 17) peptide can be separated from the binding protein by normal chromatographic methods including ion exchange, reverse phase, and size exclusion. Alternatively, the recombinant single copy polypeptide may be separated from the carrier protein by standard precipitation methods. The purified single copy recombinant GRF (1–41)-Ala-Arg-Leu-Ala (SEQ ID NO: 17) is then treated according to the method of invention, as previously described in the presence of an Ala-Arg-Leu-NH$_2$ or Ala-Arg-Leu-Gly (SEQ ID NO:8) addition units to yield the modified recombinant products GRF (1–44)-NH$_2$ (SEQ ID NO: 16) and GRF (1–44)-Gly (SEQ ID NO: 21).

3. Thrombin Transpeptidation of a Multicopy Recombinant Polypeptide

In a third variation, according to a method of the invention, thrombin may be used to simultaneously cleave and transpeptidate a recombinant multicopy polypeptide to form the desired modified recombinant polypeptide product. In this variation, the recombinant multicopy polypeptide is produced by methods discussed Section II. The multiple single copy recombinant GRF (1–41) (SEQ ID NO: 7) cores are linked together without the use of an intraconnecting peptide. The terminal GRF (1–41) (SEQ ID NO: 7) core is linked to an -Ala-leaving unit. The GRF (1–41) (SEQ ID NO: 7) linkages are prefixed by the thrombin recognition sequence -Gly-Ala-Arg- and cleavage occurs at the -Arg$^{41}$-carboxy group (see SEQ ID NO:7)

The recombinant multicopy polypeptide is purified, as discussed Section II. The number of single copy polypeptides which may be linked within the recombinant multicopy polypeptide is limited only by the physical capabilities of the expression system. The recombinant multicopy polypeptide is added to buffer solution with thrombin and an addition unit, as described above. Also as described above, the reaction may be conducted in organic solvents to favor the transpeptidation reaction.

In this variation, the thrombin recognition site of -Gly-$^{39}$-Ala$^{40}$-Arg$^{41}$ is also utilized to facilitate the cleavage of GRF (1–41)-Ala-Arg-Leu-Ala (SEQ ID NO: 17) at the -Arg$^{41}$-Ala$^{42}$-Arg$^{43}$-Leu$^{44}$-Ala$^{45}$ (SEQ ID NO: 22) linkage of the terminal single copy recombinant polypeptide. In the presence of a suitable nucleophile such as Ala-Arg-Leu-Gly-Arg-NH$^2$ or Ala-Arg-Leu-Gly (SEQ ID NO:8), the desired modified recombinant polypeptide products are produced through transpeptidation simultaneous with cleavage of the multicopy recombinant polypeptide.

4. Thrombin Transpeptidation of a Multicopy Recombinant Polypeptide Derived From a Fusion Protein Construct The modified recombinant multicopy polypeptide products may be produced, according to the method of the invention by transpeptidation of recombinant single copy core polypeptide units which have been derived from a multicopy polypeptide unit which has been derived from a fusion protein construct. The number of recombinant single copy core polypeptides included within the recombinant multicopy fusion protein construct is limited only by the physical capabilities of the expression system. Purification of the recombinant multicopy polypeptide from the fusion protein construction is as previously described. The purified recombinant multicopy polypeptide is separated from the fusion protein construct and then treated with thrombin endopeptidase enzyme, as described above, to yield the desired modified recombinant polypeptide product.

The multicopy fusion protein construct is prepared as described Section II.

II. Forming the Recombinant Single- or Multicopy Polypeptide and the Single- or Multicopy Recombinant Fusion Protein Construct The recombinant single- or multicopy polypeptide or the single- or multicopy recombinant fusion protein construct is formed by recombinant DNA methods disclosed in U.S. application Ser. No. 07/552,810, the disclosure of which is incorporated herein by reference. The gene sequence for the desired recombinant polypeptide can be cloned or, in the case of a smaller peptide, synthesized by automated synthesis. The gene sequence encoding the leaving unit is linked at the C-terminal end of the core polypeptide.

For conciseness, the term "fusion protein construct" will be used to refer to either the single- or multicopy recombinant fusion protein. The term "polypeptide construct" will be used to generically refer to the recombinant single- or multicopy polypeptide.

The expression vector containing the recombinant gene for a polypeptide construct or fusion protein construct is capable of directing expression of the recombinant gene in prokaryotic or eukaryotic cells. The expression vector incorporates the recombinant gene and base vector segments such as the appropriate regulatory DNA sequences for transcription, translation, phenotyping, temporal or other control of expression, RNA binding and post-expression manipulation of the expressed product. The expression vector generally will include structural features such as a promoter, an operator, a regulatory sequence and a transcription termination signal. The expression vector can be synthesized from any base vector that is compatible with the host cell or higher organism and will provide the foregoing features. The regulatory sequences of the expression vector will be specifically compatible or adapted in some fashion to be compatible with prokaryotic or eukaryotic host cells or higher organisms. Post-expression regulatory sequences, which cause secretion of the polypeptide construct can be included in the eukaryotic expression vector. It is especially preferred that the expression vector exhibit a stimulatory effect upon the host cell or higher organism such that the polypeptide construct is overproduced relative to the usual biosynthetic expression of the host.

Transformed prokaryotic or eukaryotic cells or higher organisms carrying the appropriate recombinant prokaryotic or eukaryotic vectors constitute the transformed cells of this invention. The prokaryotic cells useful as hosts include any that are amenable to expression of foreign protein. Preferred embodiments include *E. coli* and *B. subtilis*. The eukaryotic cells include unicellular organisms, such as yeast cells, as well as immortal cells from higher organisms, such as plant, insect or mammalian cells. Preferred eukaryotic cells include *Saccharomyces cerevisiae, Pichia pastoris, Asperaillus niger, Spodoptera frupiperda*, and corn, tobacco or soybean plant cells. The higher organisms useful as hosts include higher order plants and animals having germ cells that are amenable to transformation. Included are plants such as tobacco, corn, soybean and fruit bearing plants, and invertebrate and vertebrate animals such as fish, birds and mammals especially including sheep, goats, cows, horses and pigs.

The invention as well includes a cultured, transformed cell or transformed plants or animals that are capable of expressing the fusion protein or polypeptide construct composed of a core of at least one leaving unit, wherein the leaving unit is linked to the core by an enzyme cleavage site and may be substituted by an addition unit when transpeptidated by an endopeptidase cleavage enzyme.

The expression steps of the method according to the present invention are based upon microbial or higher organism protein expression. The steps call for inserting the recombinant gene into an appropriate base vector, transforming host cells or higher organisms with the resulting recombinant vector and expressing the polypeptide construct or fusion protein construction, preferably as a soluble product within the host cell or higher organism, as a product that is insoluble in the cell cytoplasm, or as a secreted product by the host cell or higher organism. When higher organisms are chosen as the host, fertilized germ cells of that organism are transformed and the transformed organism grown through usual maturation techniques.

The purification steps of a polypeptide construct call for separating the polypeptide construct from other cellular constituents, debris, and culture medium. The purification steps of a fusion protein construct call for affinity binding of the fusion protein construct to an immobilized ligand, and separating it from other cellular constituents, debris and culture medium. The polypeptide portion of the fusion protein construct is obtained from the immobilized fusion protein construct through enzymatic or chemical cleavage action upon the interconnecting peptide, and separating the variable fused polypeptide from the cleavage enzyme or other material. (Throughout this application, mention of enzymatic or chemical cleavage alone will be understood to include both.)

Alternatively, the purification steps can separate the entire fusion protein construct from the immobilized ligand after purification and cleave it with an immobilized cleavage enzyme or chemical reagent to produce a mixture containing the variable fused polypeptide and binding protein. This mixture can be separated by use of an immobilized ligand for the binding protein and removal of the purified polypeptide construct.

Preferred embodiments of the method include those expressing the recombinant gene composed of DNA segments for human carbonic anhydrase (or a modified functional version thereof), interconnecting peptide and a recombinant single copy polypeptide or multiple units thereof. Additional preferred embodiments include use of E. coli or yeast as the host cells and use of controlled expression by means of any induction system such as temperature, nutrients, isopropyl thiogalactoside, indole acrylic acid, carbon sources and the like, so as to allow the production of a protein purification construct that would be toxic to the host. Further preferred embodiments include use of an expression vector system for prokaryotic cells which incorporates a two plasmid construction, and an expression vector system for yeast cells which incorporates a shuttle vector with an origin of replication for E. coli and one for S. cerevisiae.

Due to E. coli digestion of single copy recombination polypeptide expressed intracellularly, incorporation into a fusion protein construct is required. The possibility of an E. coli organism, which does not degrade intracellularly expressed single copy recombinant polypeptides not attached to a carrier protein, is recognized according to the method of the invention.

A. Recombinant Polypeptide Production From a Fusion Protein Construct

1. Method For Expression of Host Cells of Fusion Protein Construct

The methods for expression of single- and multicopy recombinant fusion protein products disclosed in U.S. patent application Ser. No. 07/552,810, filed Jul. 16, 1990, the disclosure of which is incorporated herein by reference.

As discussed in U.S. Ser. No. 07/552,810, the use of multicopy or single copy recombinant fusion proteins allows for the highly efficient purification of recombinant polypeptides. The construct of a recombinant fusion protein has three tandem segments. The first segment is a binding protein which exhibits strong, reversible binding to a specific small molecular weight ligand. The second segment is an interconnecting peptide which is selectively cleavable by an enzyme or chemical technique. The interconnecting peptide connects the binding protein to the N- or C-terminal end of the recombinant single copy or multicopy polypeptide. It is typically a short chain peptide. It is preferred to construct the fusion protein construct gene so that the binding protein gene fragment is read first. The third segment, the variable fused polypeptide, incorporates any natural or synthetic polypeptide desired as a starting product for the method of the invention.

2. Method of Purification of Fusion Protein Construct

The recombinant single or multicopy polypeptide produced as a fusion protein allows for easy purification by affinity chromatography. The fusion protein produced in the transformed cells can be soluble in the cells or insoluble in inclusion bodies. Soluble fusion protein construct is obtained by lysis of the transformed cells to form a crude cell lysate. The crude cell lysate can be further purified by methods including ultrafiltration and ion exchange chromatography before purification by affinity chromatography. Insoluble fusion protein in inclusion bodies is also purified by similar methods.

To perform affinity purification, the crude mixture of materials is combined with an immobilized ligand for the binding protein. Examples of the binding protein, corresponding ligand and dissociation constants are given in Table 1. A complete discussion of the method of purification of the fusion protein construct is found in copending application Ser. No. 07/552,810, the disclosure of which is incorporated herein by reference.

TABLE 1

| Binding Protein | Ligand | Kd | Ref. |
|---|---|---|---|
| Xanthine Oxidase | Allopurinol | strong | 1 |
| Adenosine deaminase | Coformycin | <1.2E–10 | 1 |
| Adenosine deaminase | Deoxycoformycin | 2.SE–12 | 2 |
| Adenosine deaminase | erythro-9-(2-hydroxy-3 nonyl) adenine | 1.6E–9 | 2 |
| Dihydrofolate reductase | Methotrexate | 1.2E–9 | 4 |
| Dihydrofolate reductase | Methotrexate | 2.3E–9 | 5 |
| Dihydrofolate reductase | Aminopterin | 3.7E–9 | 5 |
| Dihydrofolate reductase | Trimethoprin | 4.6E–9 | 5 |
| Ribulose bisphosphate carboxylase | 2 carboxyarabirital 1,5 bisphosphate | 1E–14 | 6 |
| Pepsin | Pepstatin | 10E–9 | |
| Calmodulin | Melittin | 3E–9 | 7 |
| Calmodulin | Various peptides | 0.2E–9 | 7 |
| Cholesterol esterase | Borinic acid | 0.1E–9 | 8 |

TABLE 1-continued

| Binding Protein | Ligand | Kd | Ref. |
|---|---|---|---|
| Carbonic anhydrase II | Sulfanilamide | 4.6E−7 | 3 |
| Carbonic anhydrase II | Acetazolamide | 6E−10 | 3 |

E is times ten to the negative exponent indicated.
References Cited in Table 1
1. Cha et al., Biochemical Pharm., 24, 2187–2197.
2. Agarwal et al., Biochemical Pharm., 26, 354–367 (1977).
3. Taylor, P. W. et al., Biochemistry, 9, 2638 (1970).
4. Cha et al., Biochemical Pharm., 30, 1507–1515 (1981).
5. Williams et al., Biochemical Pharm., 29, 589–595 (1980).
6. Pierce, J., Tolbert, N. E., Barker, R., Biochem., 19:934–942 (1980).
7. Degrado et al., J. of Cellular Biochem., 29, 83–93 (1989).
8. Sutton et al., BBRC, 134, 386–392 (1986).

For the preferred carbonic anhydrase enzyme, the ligand is sulfanilamide or a benzene sulfonamide derivative. Immobilization of the ligand on a solid support can be accomplished by the methods of W. Scouter, *Methods Enzymol.*, 34, 288–294 (1974); S. Marcus, *Methods Enzymol.*, 34, 377–385 (1974); A. Matsura et al., *Methods Enzymol.*, 34, 303–4 (1974); R. Barker, *Methods Enzymol.*, 34, 317–328 (1974); I. Matsumoto, *Methods Enzymol.*, 34, 324–341 (1974), J. Johansen, *Carlsberg Res. Commun.*, 14, 73 (1976) and G. S. Bethell et al., *J. Biol. Chem.*, 254, 2572–2574 (1979); the disclosures of which are incorporated herein by reference. The fusion protein binds to the immobilized ligand through the reversible affinity of the binding protein for its ligand. The remaining constituents and debris of the crude mixture of materials can then be removed by washing or similar techniques.

Two routes can be employed for further purification of the fusion protein. According to the first route, the single or multicopy fusion protein is dissociated intact from the immobilized ligand by washing with a strong competing ligand solution. Examples include cyanides, pseudocyanides such as thiocyanides, perchlorates, halide and similar strong Lewis bases.

According to the second route, the immobilized single or multicopy fusion protein is contacted directly with cleavage reagent to release the single or multicopy polypeptide. To isolate the single or multicopy polypeptide in the second route, its mixture with cleavage enzyme can be combined with a means for molecular weight selection (e.g. partition chromatography dialysis, filtration based on molecular size or high pressure liquid chromatography on a "particle exclusion" base or ion exchange chromatography) such that the high molecular weight cleavage enzyme is separated from the free variable fused peptide. Or, the mixture can be combined with an immobilized affinity material for the cleavage enzyme.

The cleavage enzyme chosen will depend upon the interconnecting peptide chosen. Examples of cleavage enzymes and their cleavage sites are given in Table 2.

TABLE 2

| | DNA Seq. |
|---|---|
| Enzymes for Cleavage | |
| Enterokinase | GACGACGACGATAAA (SEQ ID NO:10) |
| Factor Xa | ATTGAAGGAAGA (SEQ ID NO:11) |
| Thrombin | AGAGGACCAAGA (SEQ ID NO:12) |

TABLE 2-continued

| | DNA Seq. |
|---|---|
| Ubiquitin Cleaving Enzyme | AGAGGAGGA (SEQ ID NO:13) |
| Renin | CATCCTTTTCATCTGCTGGTTTAT (SEQ ID NO:14) |
| Trypsin | AAA OR CGT |
| Chymotrypsin | TTT or TAT or TGG |
| Clostripain | CGT |
| *S. aureus* V8 | GAA |
| Chemical Cleavage | |
| (at pH3) | GATGGA |
| (Hydroxylamine) | AATCCA |
| (CNBr) | ATG |
| BNPS-skatole | TGG |
| 2-Nitro-5-thiocyanobenzoate | TGT |

The purification methods described above yield the starting materials for the method of the invention: a single copy recombinant fusion protein, a multicopy recombinant fusion protein, a single copy recombinant polypeptide, or a multicopy recombinant polypeptide. In a preferred embodiment, the recombinant single and multicopy polypeptides are produced from a fusion protein.

B. Recombinant Polypeptide Production From a Recombinant Polypeptide

1. Recombinant Method For Expression of Host Cells of Multicopy Polypeptide

The method for expression of single- and multicopy recombinant polypeptide, i.e. a polypeptide expressed with a leader sequence, a limiting protein or an affinity moiety attached to it, are known in the art and described in *Protein Purification: From Mechanisms to Large-Scale Processes*, Michael Ladisch, editor; American Chemical Society, publisher (1990), the disclosure of which is incorporated herein by reference.

2. Method of Purification of Recombinant Multicopy Polypeptide

The method for purification of a recombinant multicopy polypeptide is known in the art and is described in Kirshner et al., *J. Biotechnology*, 12:247–260 (1989), the disclosure of which is incorporated herein by reference.

III. Therapeutic Use of Recombinant Modified Polypeptide Products Produced by the Method of the Invention The products of the present invention have significant therapeutic and supplemental physiological uses in clinical human and veterinary medical practice. For example, the insulinotrophic activity of GLP1 (7–36)-NH$_2$ (SEQ ID NO: 1) has been shown to be beneficial in treating the symptoms of non-insulin dependent diabetes mellitus (NIDDM, Type II). Gutniak, *New Eng. J. Med.*, 326:1316–2 (1992). GRF (1–44)-NH$_2$ (SEQ ID NO: 16) is of therapeutic benefit for diseases such as short stature syndrome, endometriosis, and osteoporosis. In addition, supplemental GRF has been used to increase the lean to fat ratio in livestock allowing production of more wholesome meat products.

Methods of preparation of pharmaceutically functional compositions of the products of the invention, in combination with a physiologically acceptable carrier, are known in the art. A functional pharmaceutical composition must be administered in an effective amount, by known routes of administration, for which the dosage is dependent on purpose for use and the condition of the recipient.

EXAMPLE 1
Preparation of Amidated Recombinantly Produced GLP1 (7–36)-NH$_2$ From a Single Copy Fusion Protein Construct The naturally occurring sequence of Glucagon Like Peptide 1 (GLP1) (SEQ ID NO:15) is:

```
His-Asp-Glu-Phe-Glu-Arg-His-Ala
1                             7

Glu-Gly-Thr-Phe-Thr-Ser-Asp-Val-Ser

Ser-Tyr-Leu-Glu-Gly-Gln-Ala-Ala

Lys-Glu-Phe-Ile-Ala-Trp-Leu
26 27

Val-Lys-Gly-Arg- NH2
      34     36
```

A GLP1 peptide is a 36 amino acid peptide that has been recombinantly produced but without a mechanism for providing for the amidation of the C-terminal arginine residue. In this example, the method of the invention has been designed to produce a single copy fusion protein construct containing one copy of a gene encoding a truncated core GLP1 and amidating the core GLP1 by a transpeptidation reaction, using the endopeptidase trypsin, to form a modified recombinant GLP1 polypeptide.

The strategy involves forming a DNA construct encoding a single copy recombinant fusion protein. The single copy fusion protein includes at least three segments. The first segment is a binding protein which exhibits strong reversible binding to a specific small molecular weight ligand. The second segment is an interconnecting peptide which is selectively cleavable by an enzyme or chemical technique. The third segment is a variable fused peptide containing one copy of the desired natural or synthetic polypeptide, in this case GLP1 (7–34) (SEQ ID NO: 4). The formation of a DNA construct for the fusion protein, as well as the fusion protein itself, has been described in copending U.S. application Ser. No. 07/552,810 filed Jul. 6, 1990, which is hereby incorporated by reference.

The single copy fusion protein can be formed with human carbonic anhydrase modified at residue 240 as the binding protein. The modification of carbonic anhydrase at residues 240 involves a substitution of a leucine for a methionine. The interconnecting peptide is a methionine residue which can be cleaved by cyanogen bromide. The variable fused polypeptide contains a single copy of a modified truncated GLP1 peptide having the following sequence (SEQ ID NO:2):

```
His-Ala-Glu-Gly-Thr-Phe-Thr-
7

Ser-Asp-Val-Ser-Ser-Tyr-Leu-Glu-

Gly-Gln-Ala-Ala-Lys-Glu-Phe-Ile-
              26 27

Ala-Trp-Leu-Val-Lys-Ala-Phe-Ala
            34          37
```

The core GLP1 peptide is truncated from the native sequence so that it contains residue corresponding to residues 7–34 of the naturally occurring sequence. The GLP1 peptide is modified by the linkage of an Ala-Phe-Ala leaving unit at residues 35–37 (SEQ ID NO: 2). This tripeptide is not found in the naturally occurring sequence and is a good leaving group for trypsin transpeptidation. Briefly, this single copy recombinant fusion protein can be produced from a DNA construct formed as follows. The DNA sequence from the human carbonic anhydrase II gene is modified so that the methionine codon at amino acid residue 240 is replaced with a leucine codon using cite directed mutagenesis, as described in Sambrook et al., *Molecular Cloning, A Laboratory Manual*, Cold Spring Harbor Laboratory, New York (1989). The modified gene for human carbonic anhydrase is then cloned into an expression vector which is compatible with *E. coli*, such as pB0304, as described in U.S. application Ser. No. 07/552,810. A nonessential preferred embodiment is a short DNA fragment including the codon for methionine is chemically synthesized and inserted immediately downstream from the end of the gene for human carbonic anhydrase by standard methods. A DNA sequence encoding the truncated core GLP1 (7–34)-Ala-Phe-Ala (SEQ ID NO: 2) polypeptide is formed by automated DNA synthesis and inserted directly downstream from the interconnecting DNA segment encoding the methionine codon. The final recombinant expression vector encoding the single copy fusion protein is transformed into *E. coli* by standard methods and the expressed recombinant single copy fusion protein can be obtained using affinity chromatography with sulfanilamide or by other chromatographic methods. Once the recombinant fusion protein is purified, it can be cleaved and transpeptidated.

Cleavage and transpeptidation can be conducted as follows. For example, a 40 mg/ml solution of HCA-Met-GLP1 (7–34)-Ala-Phe-Ala (SEQ ID NO: 2) can be digested with a 50-fold excess of cyanogen bromide (CNBr) methionine in 70% formic acid to release the GLP1 (7–34)-Ala-Phe-Ala (SEQ ID NO: 2) peptide. The reaction mixture can be incubated in the dark under oxygen-free nitrogen at 20°–25° C. for 16–24 hours. The reaction mixture is diluted with 15 volumes of water and freeze dried. For the complete removal of acid and by-products, the freeze drying can be repeated after further addition of water. This cleavage reaction yields human carbonic anhydrase and the recombinant GLP1 (7–34)-Ala-Phe-Ala (SEQ ID NO: 2) polypeptide.

The cleaved GLP1 7–34 Ala-Phe-Ala (SEQ ID NO: 2) polypeptide can be separated from human carbonic anhydrase by normal chromatographic methods, i.e., ion exchange, reverse phase, or by size exclusion. In addition, the cleaved GLP1 (7–34)-Ala-Phe-Ala (SEQ ID NO: 2) polypeptide can be separated from the human carbonic anhydrase by simple precipitation procedure. A solution containing carbonic anhydrase, 70% formic acid, cyanogen bromide, methionine, and peptide is diluted with water to a protein concentration of 20 mg/ml while maintaining an acetic acid concentration of 10%. The addition of 5.6 g/100 ml of sodium sulfate (Na$_2$SO$_4$) to this mixture results in a precipitate which can be removed by centrifugation at 10,000× g for 10 minutes. The carbonic anhydrase can be quantitatively precipitated and greater than 80% of the peptide remains in solution. The supernatant can be applied to an open C-8 column which is rinsed with four column volumes of 10% acetic acid. The GLP1 (7–34) -Ala-Phe-Ala (SEQ ID NO: 2) can be eluted from the column with 50% acetonitrile in 10% acetic acid. The peptide can then be freeze dried.

Once purified, the GLP1 (7–34)-Ala-Phe-Ala (SEQ ID NO: 2) can be transpeptidated to yield the modified recombinant native GLP1 (7–36)-NH$_2$ amino acid product as follows.

The recombinant GLP1 (7–34) -Ala-Phe-Ala (SEQ ID NO: 2) polypeptide can be cleaved with trypsin at the cleavage site between amino acid residues 34 and 35 at the Lys-Ala bond in the recombinant truncated polypeptide.

Trypsin did not cleave the Lys-Glu bond of residues 26 and 27 in experiments conducted on the recombinant GLP1 polypeptide as shown in SEQ ID NO:2. While not in any way meant to limit the invention, it is believed that cleavage at residues 26 and 27 by trypsin is not favored because of the presence of the acidic glutamic acid residue.

The cleavage with trypsin is conducted in the presence of either Gly-Ag-NH$_2$ or Gly-Arg-Gly addition units so that the cleavage of the Ala-Phe-Ala leaving unit is followed by the addition of Gly-Ag-NH$_2$ or Gly-Arg-Gly to the core GLP1 (7–34) (SEQ ID NO: 4) polypeptide to yield either amidated GLP1 (7–36)-NH$_2$ (SEQ ID NO: 1) polypeptide or GLP1 (7–36) peptide with a terminal glycine.

For example, the freeze dried GLP1 (7–34) -Ala-Phe-Ala (SEQ ID NO: 2) is dissolved at 10 mg/ml in a buffer at pH 5–11 with 0.01 to 1 M Gly-Arg-NH$_2$ or Gly-Arg-Gly leaving unit which contains bovine trypsin at a 1:1000 ratio (trypsin:peptide) at 37° C. The mixture was stirred using a magnetic stirrer at 1000 rpm. The trypsin cleaves the Ala-Phe-Ala from the carboxy terminus of the core and forms an acyl-enzyme intermediate to residue 34 of the core. The Gly-Arg-NH$_2$ or Gly-Arg-Gly acts as a nucleophile favoring transpeptidation of the acyl-enzyme intermediate. The first reaction is:

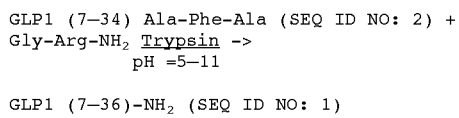

```
GLP1 (7-34) Ala-Phe-Ala (SEQ ID NO: 2) +
Gly-Arg-NH2  Trypsin  ->
             pH =5-11

GLP1 (7-36)-NH2 (SEQ ID NO: 1)
```

The second reaction is:

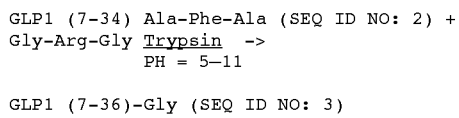

```
GLP1 (7-34) Ala-Phe-Ala (SEQ ID NO: 2) +
Gly-Arg-Gly  Trypsin  ->
             PH = 5-11

GLP1 (7-36)-Gly (SEQ ID NO: 3)
```

The production of GLP1 7–36-NH$_2$ (SEQ ID NO: 1) or GLP1 7–36-Gly (SEQ ID NO: 3) is monitored by HLPC and the reaction stopped by the addition of 2 M HCl until the pH is below 3. As described by Bongers et al., *Int. J. Peptide Protein Res.*, 40:268 (1992), the GLP1 (7–36)-Gly (SEQ ID NO: 3) can be converted to an amide in a later reaction by use of the C-terminal α-amidating enzyme as described in Ohsuye et al., cited supra.

EXAMPLE 2
Preparation of Amidated Recombinant GLP1 (7–36)-NH$_2$ From a Multicopy Fusion Protein Construct Amidated recombinant GLP1 (7–36)-NH$_2$ (SEQ ID NO: 1) was prepared from a multicopy fusion protein containing four copies of a modified truncated GLP1 peptide having amino acid residues 1–34 of the native or naturally occurring polypeptide and the terminal amino acid residues of Ala-Phe-Ala at residues 35–37 (SEQ ID NO: 2).

A DNA construct encoding a multicopy fusion protein can be prepared as described in Example 1. Briefly, a non-essential preferred embodiment is a gene encoding human carbonic anhydrase modified so that the codon for methionine at amino acid residue 240 is replaced with the codon for leucine and subcloned into a vector that can be expressed in *E. coli* such as pB0304, as described in U.S. application Ser. No. 07/552,810. The DNA sequence for the interconnecting peptide encoding a methionine residue, the DNA sequence encoding four copies of the prefixed recombinant GLP1 (1–34)-Ala-Phe-Ala (SEQ ID NO: 23) polypeptide can be synthesized by automated DNA synthesis with the methionine codon 5' to the DNA sequence encoding the truncated modified GLP1 sequence. This DNA sequence is then inserted immediately downstream from the gene for human carbonic anhydrase in the *E. coli* expression vector by standard methods. The expression vector encoding the multicopy fusion protein is then transformed into *E. coli*. Transformants are selected and amplified. The multicopy fusion protein is recovered and purified from cell lysates as described in Example 1.

Once purified, the multicopy fusion protein is cleaved with cyanogen bromide as described in Example 1 to yield human carbonic anhydrase and a multicopy protein containing four copies of the truncated GLP1 (1–34)-Ala-Phe-Ala (SEQ ID NO: 23) polypeptide. The multicopy peptide can be separated from human carbonic anhydrase by standard chromatographic methods such as ion exchange, reverse phase or size exclusion or by the precipitation method described in Example 1.

The multicopy polypeptide is then cleaved and transpeptidated with trypsin as follows. Trypsin will cleave the multicopy polypeptide into single copy polypeptides between amino acid residues 6–7 and residues 34 and 35 to yield four single copies of GLP (7–34) (SEQ ID NO: 4) and peptides containing Ala-Phe-Ala- connected to amino acid residues 1–6. When the cleavage is conducted in the presence of an appropriate nucleophilic addition unit, such as Gly-Arg-NH$_2$, transpeptidation occurs. For example, freeze dried multicopy polypeptide is dissolved at 10 mg/ml and a buffer at pH 5–11 with 0.01 to 1 ml Gly-Arg-NH$_2$ which contains trypsin at a 1:1000 ratio (trypsin:peptide). The trypsin cleaves the multicopy peptide as described above to yield GLP1 (7–34) (SEQ ID NO: 4) core polypeptide which forms an acyl-enzyme intermediate with the trypsin. The Gly-Arg-NH$_2$ acts as a nucleophile and transpeptidation occurs at amino acid residue 34. The production of GLP1 (7–36)-NH$_2$ (SEQ ID NO: 1) is monitored by HPLC and the reaction stopped by the addition of HCl when the reaction has reached completion.

EXAMPLE 3
Preparation of Amidated Recombinantly Produced GLP1 (7–36) NH$_2$ From a Multicopy Polypeptide Modified recombinant GLP1 (7–36)-NH$_2$ (SEQ ID NO: 1) can also be prepared by cleavage and transpeptidation of a multicopy polypeptide. The multicopy polypeptide was formed with four copies of core GLP1 (7–34) (SEQ ID NO: 4) connected to a terminal core GLP1 (7–34) linked to a Ala-Phe-Ala leaving unit (SEQ ID NO: 2).

A DNA construct encoding the recombinant multicopy polypeptide can be formed as described for a multicopy or single copy recombinant fusion protein as described in Examples 1 and 2, but without the carbonic anhydrase as fusion protein or the methionine codon as interconnecting peptide. A DNA sequence encoding four copies of the GLP1 (7–34) (SEQ ID NO: 4) core polypeptide and a terminal GLP1 (7–34) -Ala-Phe-Ala (SEQ ID NO: 2) recombinant polypeptide can be synthesized by automated DNA synthesis. The DNA sequence is then subcloned into an expression vector compatible with *E. coli* and transformed into *E. coli*. Transformants expressing the recombinant multicopy polypeptides were selected and amplified. It is likely that the recombinant multicopy polypeptide will be found in inclusion bodies. The recombinant multicopy polypeptide can be purified from inclusion bodies as follows.

Cells are lysed with sonication in 50 ml Tris-Hcl (pH=7.9) and 2.5 ml EDTA containing 100 mM NaCl with 10 micrograms of DNase 1. Lysozyme (30 ml) is added and the lysate is incubated overnight to disrupt the cell fragments. To purify recombinant polypeptide from insoluble granules, the lysate is then centrifuged and the insoluble granules are incubated with sodium deoxycholate, and washed several times. The inclusion bodies are then frozen. The thawed inclusion bodies are further purified by ultrafiltration and DEAE chromatography after being dissolved in an appropriate chaotropic reagent, such as urea, guanidine, or 50 mM NaOH.

Once purified, the recombinant multicopy polypeptide is cleaved and transpeptidated with trypsin. Trypsin will cleave at the -Lys- at residue 34 to yield single copies of the core GLP1 (7–34) (SEQ ID NO: 4) and a copy of a GLP1 (7–34)-Ala-Phe-Ala (SEQ ID NO: 2). The GLP1 (7–34)-Ala-Phe-Ala (SEQ ID NO: 2) will also be cleaved by trypsin to yield GLP1 (7–34) (SEQ ID NO: 4) core and the leaving unit Ala-Phe-Ala. The trypsin cleavage of the multicopy polypeptide is conducted in the presence of a nucleophilic addition unit such as Gly-Arg-NH$_2$ so that the final product is a GLP1 (7–36) -NH$_2$ (SEQ ID NO: 1) Modified recombinant polypeptide as a result of trypsin catalyzed transpeptidation.

EXAMPLE 4
Preparation of Amidated Recombinant Growth Hormone Releasing Factor (GRF) (1–44)-NH$_2$ From a Fusion Protein Construct A modified recombinant growth hormone releasing factor can be prepared by cleavage and transpeptidation of a recombinant multicopy fusion protein. The native or naturally occurring sequence of growth hormone releasing factor (SEQ ID NO: 16) is:

```
Tyr-Ala-Asp-Ala-Ile-Phe-Thr-Asn-Ser-Tyr-Arg-Lys-
1

Val-Leu-Gly-Gln-Leu-Ser-Ala-Arg-Lys-Leu-Leu-Gln
13

Asp-Ile-Met-Ser-Arg-Gln-Gln-Gly-Glu-Ser-Asn-Gln
25

Glu-Arg-Gly-Ala-Arg-Ala-Arg-Leu-NH₂
37                                44
```

A recombinantly produced growth hormone releasing factor (GRF) is not produced in the highly active amidated form and an additional step using an α-amidating enzyme is typically necessary. However, a strategy can be designed to form the amidated GRF by combining cleavage of a recombinant single copy fusion protein with transpeptidation.

A DNA construct encoding a single copy fusion protein can be formed as described in Example 1. Briefly, the gene for human carbonic anhydrase is subcloned into a E. coli expression vector such as pB0304, as described in U.S. application Ser. No. 07/552,810. The DNA sequence encoding an interconnecting peptide of the following sequence (SEQ ID NO:9):

Asn-Gly-Pro-Arg is synthesized by automated DNA synthesis. A DNA sequence encoding a truncated core GRF polypeptide and the leaving unit -Ala-, for example GRF (1–41)-Ala-Arg-Leu-Ala, having the following sequence (SEQ ID NO: 17):

```
Tyr-Ala-Asp-Ala-Ile-Phe-Thr-Asn-Ser-Tyr-Arg-Lys-
1

Val-Leu-Gly-Gln-Leu-Ser-Ala-Arg-Lys-Leu-Leu-Gln-
13

Asp-Ile-Met-Ser-Arg-Gln-Gln-Gly-Glu-Ser-Asn-Gln
25

Glu-Arg-Gly-Ala-Arg-Ala-Arg-Leu-Ala
37             41            45
``` is synthesized by automated DNA synthetic methods. The terminal Ala-residue is added because it serves as a good leaving unit for the cleavage and transpeptidation reaction. The DNA sequence for the interconnecting peptide and the truncated modified GRF (1–41)-Ala (SEQ ID NO: 24) peptide can be synthesized together as a single sequence or separately and then subcloned immediately downstream from the gene for human carbonic anhydrase to form the expression vector for the fusion protein. The expression vector is then transformed into E. coli and transformants are selected and amplified. The fusion protein is isolated and purified from cell lysates using affinity chromatography as described in Example 1.

Once purified, the human carbonic anhydrase fusion protein is digested with 2 M NH$_2$OH, and 5 M guanidine hydrochloride to release the GRF (1–41)-Ala-Arg-Leu-Ala (SEQ ID NO: 17) peptide from the fusion protein. The cleaved GRF 1–41-Ala-Arg-Leu-Ala (SEQ ID NO: 17) peptide can be separated from human carbonic anhydrase by normal chromatographic methods, i.e. ion exchange, reverse phase and size exclusion. Alternatively, the peptide can be separated from the carrier protein by dilution of the reaction mixture with water and acetic acid so that the concentration of acetic acid is made at 10% volume/volume (v/v). The addition 5.6 g/100 ml sodium sulfate (Na$_2$SO$_4$) to this mixture results in a precipitate which can be removed by centrifugation at 10,000×g for 10 minutes. The human carbonic anhydrase is selectively precipitated from the reaction mixture. The supernatant is applied to an open C-8 column which is rinsed with four column volumes of 10% acetic acid and the peptide is eluted from the column with 50% acetonitrile in 10% acetic acid. The peptide is then freeze dried.

For cleavage and transpeptidation, the purified GRF 1–41-Ala (SEQ ID NO: 24) peptide is then cleaved with thrombin in the presence of either Ala-Arg-Leu-NH$_2$ or Ala-Arg-Leu-Gly (SEQ ID NO:8). The purified GRF (1–41)-Ala (SEQ ID NO: 24) is dissolved at 10 mg/ml in a buffer at pH 5–11 with 0.01 to 1 M Ala-Arg-Leu-Gly-NH2 or Ala-Arg-Leu-Gly (SEQ ID NO:8) which contains thrombin at a 1:3000 ratio (thrombin:peptide). It has been discovered that the GAR sequence at residues 39–41 in the GRF (1–41) peptide (SEQ ID NO:7) is a site recognized and cleaved by thrombin. The thrombin cleaves the Ala from the carboxyl terminus and forms an acyl-enzyme intermediate. The Ala-Arg-Leu-NH$_2$ or Ala-Arg-Leu-Gly (SEQ ID NO:8) act as a nucleophile and transpeptidation occurs as follows:

Reaction 1

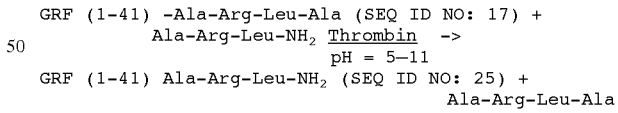

Reaction 2

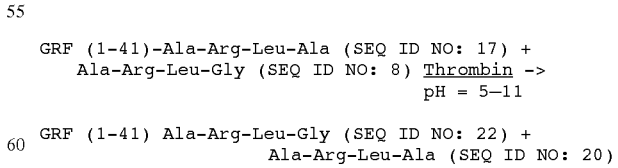

The final product of reaction 1 corresponds to the amidated native GRF (1–44)-NH$_2$ (SEQ ID NO: 16). The final product of reaction 2 corresponds to GRF (1–44)-Gly (SEQ ID NO: 21). The GRF (1–44)-Gly (SEQ ID NO: 21) can be converted to the amide by later reaction using a C-terminal α-amidating enzyme.

EXAMPLE 5
Preparation of Amidated GRF (1–44)-NH$_2$ From a Recombinant Multicopy Polypeptide Amidated recombinant GRF (1–44)-NH$_2$ (SEQ ID NO: 16) can be prepared from a recombinant multicopy polypeptide by cleavage and transpeptidation.

The recombinant multicopy peptide is produced by cells transformed with an expression vector. A DNA construct is formed by joining four copies of the coding sequence for a truncated GRF (1–41) (SEQ ID NO: 7) joined end to end and having a terminal DNA sequence encoding a modified truncated GRF (1–41)-ala (SEQ ID NO: 24) peptide. This DNA construct is formed by automated DNA synthesis and subcloned into a E. coli expression vector such pB0304. The expression vector is then transformed into E. coli and transformants are selected and then amplified. The multicopy polypeptide is isolated from cell lysates as described in Example 3.

Once purified, the multicopy polypeptide is cleaved and transpeptidated with thrombin. Thrombin cleaves after the GAR sequences of residues 39–41 in the GRF (1–41) (SEQ ID NO: 7) peptide to yield single copies of truncated GRF (1–41) (SEQ ID NO: 7) and a modified truncated GRF (1–41)-Ala (SEQ ID NO: 24). The modified truncate GRF (1–41)-Ala (SEQ ID NO: 24) is also cleaved by thrombin to yield GRF (1–41) (SEQ ID NO: 7) and alanine. The cleavage with thrombin is conducted in the presence of Ala-Arg-Leu-NH$_2$. The Ala-Arg-Leu-NH$_2$ acts as a nucleophile resulting in transpeptidation as follows:

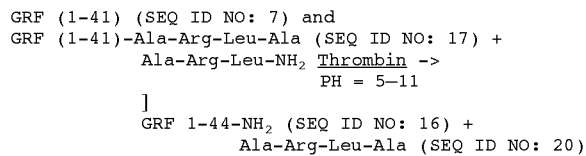

```
GRF (1-41) (SEQ ID NO: 7) and
GRF (1-41)-Ala-Arg-Leu-Ala (SEQ ID NO: 17) +
         Ala-Arg-Leu-NH2  Thrombin ->
                          PH = 5-11
     ]
     GRF 1-44-NH2 (SEQ ID NO: 16) +
              Ala-Arg-Leu-Ala (SEQ ID NO: 20)
```

The final product is amidated native GRF (1–44)-NH$_2$ (SEQ ID NO: 16).

All publications and patent applications in this specification are indicative of the level of ordinary skill in the art to which this invention pertains. All publications and patent applications are herein incorporated by reference to the same extent as if each individual publication or patent application was specifically and individually indicated by reference.

It will be apparent to one of ordinary skill in the art that many changes and modifications can be made in the invention without departing from the spirit or scope of the appended claims.

---

What is claimed is:

1. A polypeptide comprising multiple copies of contiguously linked GRF(1–41) (SEQ ID NO: 7) [GRF 1–41, wherein the terminal]and having a C-terminal GRF(1–41) (SEQ ID NO: 7) copy linked to a leaving unit.

2. A recombinant gene containing a DNA sequence coding for a polypeptide of at least one leaving unit and a core wherein the leaving unit is linked to the core by an enzyme cleavage site which is recognized by an endopeptidase enzyme, the enzyme being capable of causing the substitution of an addition unit for the leaving unit.

3. A method for treating diabetes mellitus type II comprising: administering an effective amount of GRF(1–44)-$NH_2$, wherein said GRF(1–44)-$NH_2$ is prepared by contacting (a) a polypeptide, which includes a leaving unit linked to a core by an enzyme cleavage sites and (b) an addition unit with (c) thrombin to cleave the leaving unit from the core at the enzyme cleavage site and produce a modified peptide having the addition unit attached to the core, wherein said core comprises an amino acid sequence corresponding to GRF(1–41) (SEQ ID NO: 7) and said enzyme cleavage site includes Gly-Ala-Arg.

4. A pharmaceutical composition comprising an effective amount of GRF(1–44)-$NH_2$ and a physiologically acceptable carrier, wherein said GRF(1–44)-$NH_2$ is prepared by contacting (a) a polypeptide, which includes a leaving unit linked to a core by an enzyme cleavage site, and (b) an addition unit with (c) thrombin to cleave the leaving unit from the core at the enzyme cleavage site and produce a modified peptide having the addition unit attached to the core, wherein said core comprises an amino acid sequence corresponding to GRF(1–41) (SEQ ID NO: 7) and said enzyme cleavage site includes Gly-Ala-Arg.

5. A method for treating short stature syndrome, endometriosis and osteoporosis in a patient, comprising administering to said patient an effective amount of GRF (1–44)-$NH_2$, wherein said GRF(1–44)-$NH_2$ is prepared by contacting (a) a polypeptide, which includes a leaving unit linked to a core by an enzyme cleavage site, and (b) an addition unit with (c) thrombin to cleave the leaving unit from the core at the enzyme cleavage site and produce a modified peptide having the addition unit attached to the core, wherein said core comprises an amino acid sequence corresponding to GRF(1–41) (SEQ ID NO: 7) and said enzyme cleavage site includes Gly-Ala-Arg.

6. The recombinant gene of claim 2, wherein said polypeptide comprises multiple copies of contiguously linked GRF(1–41) (SEQ ID NO: 7) and having a C-terminal GRF(1–41) (SEQ ID NO: 7) copy linked to a leaving unit.

7. The recombinant gene of claim 2, wherein said polypeptide comprises multiple copies of contiguously linked GLP1(7–34) (SEQ ID NO: 4) and having a C-terminal GLP1(7–34) (SEQ ID NO: 4) copy linked to a leaving unit.

8. An expression vector comprising the recombinant gene of claim 2.

9. An expression vector comprising the recombinant gene of claim 6.

10. An expression vector comprising the recombinant gene of claim 7.

11. A transformed cell comprising the expression vector of claim 8.

12. A transformed cell comprising the expression vector of claim 9.

13. A transformed cell comprising the expression vector of claim 10.

14. The transformed cell of claim 11, wherein said transformed cell comprises a prokaryotic cell.

15. The transformed cell of claim 14, wherein said prokaryotic cell is an *E. coli*.

16. The transformed cell of claim 11, wherein said transformed cell comprises an eukaryotic cell.

* * * * *